United States Patent
Giuliani (10) Patent No.: US 9,666,420 B2
(45) Date of Patent: May 30, 2017

(54) SYSTEM AND METHOD OF DETECTION AND QUANTIFICATION BY MASS SPECTROMETRY AND BY ACTIVATING IONISED MOLECULAR SPECIES

(71) Applicant: INSTITUT NATIONAL DE LA RECHERCHE AGRONOMIQUE—INRA, Paris (FR)

(72) Inventor: Alexandre Giuliani, Paris (FR)

(73) Assignee: Alexandre Giuliani, Paris (FR)

( * ) Notice: Subject to any disclaimer, the term of this patent is extended or adjusted under 35 U.S.C. 154(b) by 0 days.

(21) Appl. No.: 14/898,220

(22) PCT Filed: Jun. 24, 2014

(86) PCT No.: PCT/FR2014/051576
§ 371 (c)(1),
(2) Date: Dec. 14, 2015

(87) PCT Pub. No.: WO2014/207367
PCT Pub. Date: Dec. 31, 2014

(65) Prior Publication Data
US 2016/0141165 A1      May 19, 2016

(30) Foreign Application Priority Data
Jun. 24, 2013   (FR) ..................... 13 56015

(51) Int. Cl.
*H01J 49/00*       (2006.01)
*G01N 33/68*       (2006.01)
(Continued)

(52) U.S. Cl.
CPC ...... *H01J 49/0077* (2013.01); *G01N 33/6848* (2013.01); *H01J 49/0031* (2013.01);
(Continued)

(58) Field of Classification Search
None
See application file for complete search history.

(56) References Cited

U.S. PATENT DOCUMENTS 7,550,718 B2 * 6/2009 McLuckey ......... G01N 33/6848
                                                250/282
8,927,295 B2 * 1/2015 Hassell ............... H01J 49/0072
                                                436/173
(Continued)

FOREIGN PATENT DOCUMENTS

WO    WO 2015145124 A1 * 10/2015   ......... H01J 49/0045

OTHER PUBLICATIONS

Antoine et al., "Visible and ultraviolet spectroscopy of gas phase protein ions," Phys. Chem. Chem. Phys. 2011, 13, 16494-16509.
(Continued)

*Primary Examiner* — Jack Berman
(74) *Attorney, Agent, or Firm* — Young & Thompson (57) ABSTRACT

Disclosed is a system and method of mass spectrometry, including: a. ionizing an analyte to form a precursor ion (A) having a mass-to-charge ratio (m/z), in which m represents the mass and z the electric charge number; b. activating the precursor ion (A) by interaction with a beam of neutral species, ions, electrons or photons, having an energy chosen on the basis of the physicochemical properties of the precursor ion, the activation being suitable for producing a product ion (B, C) having the same mass m as the precursor ion (A) and an electric charge number z' such that z' is a non-zero integer different from z; c. separating the product ion (B, C, E, F) having a predefined mass-to-charge ratio (m/z'); d. detecting the product ion (B, C) having the predefined mass-to-charge ratio (m/z').

20 Claims, 4 Drawing Sheets

(51) Int. Cl.
    *H01J 49/42*     (2006.01)
    *G01N 30/72*     (2006.01)

(52) U.S. Cl.
    CPC ...... *H01J 49/0045* (2013.01); *H01J 49/0054* (2013.01); *H01J 49/0072* (2013.01); *H01J 49/4225* (2013.01); *G01N 30/7266* (2013.01)

(56) References Cited

U.S. PATENT DOCUMENTS

| | | | |
|---|---|---|---|
| 2005/0279931 A1* | 12/2005 | Franzen | H01J 49/0077 250/290 |
| 2014/0175276 A1* | 6/2014 | Giuliani | H01J 49/0031 250/282 |
| 2016/0268113 A1* | 9/2016 | Brown | H01J 49/00 |

OTHER PUBLICATIONS

Brunet et al., "Formation and Fragmentation of Radical Peptide Anions: Insights from Vacuum Ultra Violet Spectroscopy," J. Am. Soc. Mass Spectrum. (2012), 23:274-281.

Giuliani et al., "Structure and Charge-State Dependence of the Gas-Phase Ionization Energy of Proteins," Angew. Chem, Int, Ed. 2012, 51, 9552-9556.

Kalli et al., "Electron capture dissociation of highly charged proteolytic peptides from Lys N, Lys C and Glu C digestion," Mol. BioSyst., 2010, 6, 1668-1681.

Zubarev et al., "Multiple Soft Ionization of Gas-Phase Proteins and Swift Backbone Dissociation in Collisions with 99eV Electrons," Angew. Chem. Int. Ed. 2010, 49, 1439-1441.

\* cited by examiner

SYSTEM AND METHOD OF DETECTION AND QUANTIFICATION BY MASS SPECTROMETRY AND BY ACTIVATING IONISED MOLECULAR SPECIES

The present invention relates to the field of mass spectrometry. More precisely, the invention relates to a method of quantitative measurement of ionised molecular species by mass spectrometry.

Mass spectrometry is a technic of analysis of compounds, in particular in a mixture, which allows the detection, the identification and, under certain conditions, the quantification of ionised molecular species, even in very little quantity.

A conventional mass spectrometer comprises a source of ionisation, one or several mass analysers and an ion detection system. The source of ionisation allows to generate ionised species in gaseous phase from a sample to be analysed. The mass analyser allows to separate the ionised species as a function of their mass-to-charge ratio (m/z), where m represents the mass of the ionised species and z the electric charge number thereof. The ion detection system receives the ionised species hence separated by the mass analyser. A mass spectrum is obtained by recording the abundance of the ions as a function of their mass-to-charge ratio.

In the case where the separation of the ions as a function of the m/z ratio is performed only once, it is talked about simple mass spectrum or MS. Successive separations of the ions through several steps of tandem mass spectrometry, called $MS^n$, where n represents the level of separation, may also be performed. In this embodiment, the ionised species coming from the source of ionisation are subjected to a first step of ion separation in which one or several ions of interest are selected. This selection is performed by a mass analyser or a device allowing to select a particular domain of m/z ratio. The selected ion(s) are then subjected to a step of activation. Non-exclusively, this activation is conventionally made through collisions with an inert gas (nitrogen, argon . . . ), called CID for Collision Induced Dissociation and/or by photo-dissociation (see for example WO2012/066261_A1). The activation of the ionic species of interest, called precursors, may lead to their fragmentation and generate fragment ions whose m/z ratio is different from that of the precursors, the mass of the fragment ion being lower than that of the precursor ion. The step of selection and fragmentation may be repeated n times, either spatially in as many mass analysers in series, or temporally in an ion trap.

In simple MS mode, the m/z ratio is characteristic of the species of interest. In the $MS^2$ or MS/MS mode, to the m/z ratio of the species of interest is added another criterion, which is the mass spectrum of the fragment ions produced by the activation of the precursor (see for example WO2006/046132_A1). In the $MS^n$ tandem mass spectrometry modes, all the mass spectra obtained at all the n levels of fragmentation are taken into account in the analysis of the precursor.

The dosing of a species of interest by spectrometry may be performed in simple MS mode, as follows:
the signal received by the ion detector is proportional to the quantity of ions in the mass analyser,
the quantity of ions stemming from the mass analyser is proportional to the quantity of ions produced by the ion source,
the quantity of ions produced by the ion source is proportional to the sample quantity present in the solution.

Hence, the abundance of the ions on a simple mass spectrum may be linked to the quantity of species of interest present in the sample. In the case where it is proceeded to a chromatographic separation upstream from the ion source, the integration of the chromatographic peak corresponding to the species of interest is then linked to the quantity of this species in the sample. Nevertheless, the simple MS dosing has drawbacks. In particular, the presence of interfering ions having the same m/z ratio or a m/z ratio very close to that of the species of interest may disturb or even prevent the measurement. Indeed, the m/z ratio is not a criterion selective enough per se.

Methods based on the tandem mass spectrometry have been developed to compensate for this lack of selectivity. The SRM mode, for Single Reaction Monitoring, is based on the use of the MS/MS. In this mode, the mass-to-charge ratio of the species of interest is selected in a first step of tandem mass spectrometry, then activated for example by means of collisions with a gas. This activation leads to the fragmentation of the precursor and to the appearance of fragment ions that are specific to the precursor and that have a ratio m1/z1 different from the ratio m/z of the precursor. We call "transition" a particular way of fragmentation of the precursor towards a specific fragment: $m/z \rightarrow m1/z1$. In the SRM mode, only the signal of a specific fragmentation is followed up. Hence, in SMR mode, the abundance of a specific fragment ion is proportional to the quantity of the species of interest initially present in the sample. The SRM mode strongly increases the specificity of the measurement by very strongly reducing the contribution of spurious species. The specificity of the measurement may still be increased through several transitions. It is then talked about an MRM mode, for Multiple Reaction Monitoring. Nevertheless, in the case of very complex matrices, it may occur that compounds having a m/z ratio similar to that of the species of interest produce transitions of mass-to-charge ratio that are close enough to that which is followed up to disturb the measurement. This case is met in particular in the case of the dosage of proteins. Indeed, the protein analysis by SRM or MRM involves a step of digestion by proteolysis of the sample containing the protein that is desired to be dosed, because the entire proteins do not lend themselves to the SRM analysis. Indeed, the fragmentation of molecular ions of great size is very difficult. This digestion produces peptides for which particular transitions will be followed up by SRM or MRM analysis. Generally, peptides produce fragmentations that are more complex than those of the small molecules (metabolites, drugs . . . ), which complicates the choice of the SRM transitions. Moreover, the presence of other proteins in the sample may lead to the appearance of peptides that will produce transitions identical or very close to those that are followed up and that will disturb the measurement [see P. Picotti and R. Aebersold, 2012, "Selected reaction monitoring-based proteomics: workflows, potential, pitfalls and future directions", Nature Methods, 9 555-66]. The publication "Electron capture dissociation of highly charged proteolytic peptides from Lys N, Lys C and Glu C digestion" A. Kalli and K. Hakansson, Mol. Biosyst., 2010, 6, 16668-1681 describes the application of a technique of fragmentation by electron capture (ECD) applied to peptide ions stemming from the digestion of proteins, which leads to the scission of the peptide ions into many fragments or residues of peptides.

Figure 1:
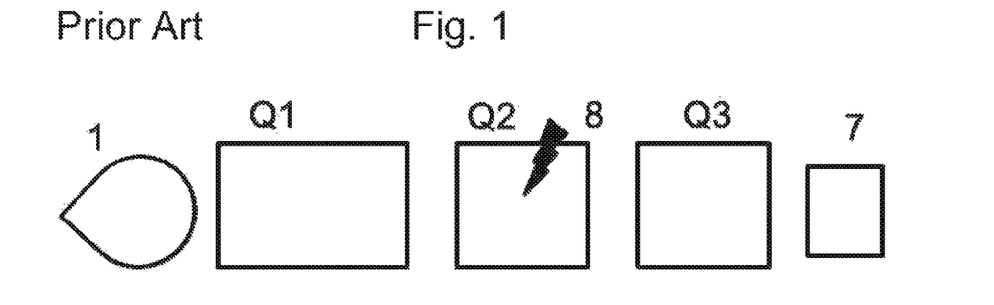
FIG. 1 schematically shows a method of analysis by mass spectrometry according to the prior art.

FIG. 1 schematically shows a triple-quadrupole mass spectrometer system as an example of apparatus for tandem mass spectrometry analysis. The system of FIG. 1 comprises a source of ionisation 1, a first mass analyser Q1, a second mass analyser Q2 coupled to an ion activation means 8, another mass analyser Q3 and an ion detection system 7. The most commonly used ion activation method is called collision induced fragmentation, or CID for Collision Induced Dissociation. The CID consists in fragmenting the ions by inelastic collision between the ions and neutral species, such as the atoms or molecules of a rare gas (helium, nitrogen, argon . . . ). However, the CID produces a non-selective fragmentation of the ions: all the ions present in the ion trap may be fragmented by collision with the collision rare gas. In SRM or MRM mode, the analyser Q1 of FIG. 1 lets through the ions corresponding to the species of interest as a function of their ratio m/z. The analyser Q2 receives these ions and fragments them into product-ions. The so-generated fragment-ions are transmitted to the analyser Q3, where they are filtered and selected as a function of their specific ratio m/z. The abundance of the fragment-ions that pass through Q3 is then recorded by the detector. This type of analysis may be made using other instrumental configurations (hybrid analysers, ion traps . . . ).

Recently, a method has appeared, in which the activation is based on the absorption of an electromagnetic wave coming from a laser by ions stored in a trap [Lemoine J, Dugourd P, Salvador A, Antoine R and Bretonniere Y (2010), patent FR 2 967 780]. This activation by absorption of a laser radiation (called LID for Laser Induced Dissociation) allows, in principle, a selective activation as a function of the emission wavelength of the laser. Indeed, the wavelength of the laser may be chosen so that only the species of interest absorbs the electromagnetic radiation. Hence, the fragmentations produced by LID are specific to the species of interest. The compounds present in the mixture can no longer interfere in the SRM (or MRM) analysis because they do not absorb the specific electromagnetic radiation. The laser induced fragmentation is made selective by the characteristics of the radiation absorption.

A major drawback of the SRM (or MRM) dosing is that it involves one or several fragmentations of the ions of interest into fragments of smaller size. The techniques of mass spectrometry analysis by Single Reaction Monitoring (SRM) and Multiple Reaction Monitoring (MRM) are not applicable if the species of interest cannot be fragmented. It is difficult, or even impossible, to fragment certain molecular species, in particular by CID. By way of non-restrictive example, the biopolymers in general and the proteins in particular cannot be subjected intact and entire to an analysis of this type. Indeed, the fragmentation of the entire proteins or biopolymers is very difficult and gives a few fragments when their size increases. That explains why a step of digestion of the proteins is implemented before the mass spectrometry analysis.

Hence, there exists a need for a method of quantitative and selective measurement by mass spectrometry.

One of the objects of the invention is to propose a mass spectrometry method allowing to overcome the limitations of the SRM and MRM techniques, allowing in particular the direct and selective analysis of intact molecular species and (bio)polymers, in particular molecular species that are difficult or even impossible to fragment.

The present invention has for object to remedy the abovementioned drawbacks of the state of the art and more particularly relates to a method for mass spectrometry measurement of ionised molecular species in a complex mixture.

According to the invention, the method comprises the following steps:

a. ionising an analyte in a complex mixture to form a precursor ion of an ionised species of interest and at least one interfering ion coming from the complex mixture, the precursor ion of said ionised species of interest and said at least one interfering ion having a same mass-to-charge ratio m/z, where m represents the mass and z the electric charge number of the precursor ion of said ionised species of interest;

b. activating the precursor ion of said ionised species of interest and of the at least one interfering ion of same mass-to-charge ratio, by interaction with a beam of neutral species, ions, electrons or photons having a predetermined energy as a function of the energy of ionisation of the precursor ion of said ionised species of interest or of the energy required for the detachment of electron from the precursor ion of said ionised species of interest, said activation being adapted to produce a product-ion, by charge transition with no fragmentation of the precursor ion of said ionised species of interest, the product-ion having the same mass m as the precursor ion of said ionised species of interest and an electric charge $z'$ such that $z'$ is a non-zero integer number different from z, $z'$ being preferably chosen among $z+1$, $z+2$, $z+3$, $z-1$, $z-2$, $z-3$, according to the polarity of the precursor ion, so that the product-ion of said ionised species of interest has a mass-to-charge ratio $m/z'$ different from the mass-to-charge ratio of the product-ion(s) stemming from the activation of the at least one interfering ion;

c. separating the product-ion of the ionised species of interest having said predetermined mass-to-charge ratio $m/z'$ specific to the ionised species of interest;

d. selectively detecting the product-ion of the ionised species of interest having said predetermined mass-to-charge ratio $m/z'$ specific to the ionised species of interest.

Therefore, the method of the invention allows to analyse by mass spectrometry and to detect one or several ions having undergone one or several charge transitions without requiring a fragmentation of the precursor ions, hence with no modification of the mass of the precursor ion of the ionised species of interest. The method of the invention allows to analyse by mass spectrometry ionised molecular species whose fragmentation is difficult or even impossible.

According to a particular and advantageous embodiment, the method further includes an additional step e) after the step d), the step e) comprising a measurement of the abundance of the product-ion having said predetermined mass-to-charge ratio $m/z'$ specific to the ionised species of interest.

According to a particular and advantageous embodiment, said precursor ion of the ionised species of interest has a positive polarity and the step b) of activation comprises a step of ionisation with no fragmentation by interaction with a beam of photons, electrons or ions so as to form a product-ion having the same mass m as said precursor ion of the ionised species of interest and a positive polarity such that the electric charge number $z'$ of the product-ion is preferably equal to $z+1$ by simple ionisation, or respectively to $z+2$ by double successive or direct ionisation.

According to a particular and advantageous embodiment, said precursor ion of the ionised species of interest has a negative polarity and the step b) of activation comprises a step of detachment of electron(s) with no fragmentation by interaction with a beam of photons or electrons, so as to produce a product-ion having the same mass m as said precursor ion of the ionised species of interest and a negative polarity such that the electric charge number $z'$ of the product-ion is preferably equal to $z-1$ by simple electron detachment, or respectively to $z-2$ by double successive or direct electron detachment.

According to a particular and advantageous embodiment, said precursor ion of the ionised species of interest has a positive polarity, with z higher than or equal to 2, and the step b) of activation comprises a step of electron capture or of electron transfer with no fragmentation by interaction with an electron beam of suitable energy so as to produce a product-ion having the same mass m as said precursor ion of the ionised species of interest and a positive polarity such that the electric charge number z' of the product-ion is preferably equal to z−1 by simple electron capture or transfer, or respectively to z−2 by double electron capture or transfer.

According to a particular and advantageous embodiment, said precursor ion of the ionised species of interest has a positive polarity, and the step b) of activation comprises a step of electron transfer with no fragmentation by interaction with a reactive anion of suitable electronic affinity so as to form a product-ion having the same mass m as said precursor ion of the ionised species of interest and a positive polarity such that the electric charge number z' of the product-ion is preferably equal to z−1 by simple electron capture, or respectively to z−2 by double electron capture.

According to a particular and advantageous embodiment, said precursor ion of the ionised species of interest has a negative polarity, and the step b) of activation comprises a step of electron transfer with no fragmentation by interaction with a reactive positive ion beam, so as to produce a product-ion having the same mass m as said precursor ion of the ionised species of interest and a negative polarity such that the electric charge number z' of the product-ion is preferably equal to z−1 by simple electron transfer, or respectively to z−2 by double electron transfer.

According to a particular and advantageous embodiment, the method of measurement further comprises the following steps:
a step a1) after the step a) of ionisation, the step a1) comprising the detection and the recording of a reference simple mass spectrum;
a step c1) of detection and recording of a tandem mass spectrum relating to a reference precursor ion of ratio $(m/z)_{ref}$ giving at least one product-ion of mass-to-charge ratio (m/z); and
a step d1) of measurement of the abundance of the product-ion of the ionised species of interest.

According to particular aspects of the method of measurement of the invention:
the step b) of activation is performed by interaction of a precursor ion with a photon beam coming from a laser, a discharge lamp or a source of synchrotron radiation or an electron beam;
the step b) of activation is performed by interaction of a precursor ion with a photon beam having a wavelength comprised in the UV or VUV domain, preferably comprised between 3 eV and 20 eV or between 3 eV and 40 eV;
the step b) of activation is performed by interaction of a precursor ion with an electron beam having a kinetic energy comprised between 0 and 100 eV;
the step b) of activation is performed by interaction of a precursor ion with an electron beam stemming from an electron gun (filament, cathode . . . ); in the case where it is searched to produce an electron capture, the energy of the electron beam is relatively low (<1 eV) and, in the case where the ionisation or the electron detachment is searched, the energy of the electrons is higher, typically from 10 eV to 100 eV, or to 10 keV;
the step b) of activation is performed by interaction of a precursor ion with a cation beam having an energy higher than 1 keV;
the method optionally comprises a previous step of fragmentation before the step b) of ionisation, of electron detachment, of electron transfer or capture with no fragmentation;
the steps b) of activation and c) of separation of a product-ion are performed in an ion trap.

Those values of energy of photons, ions or electrons are herein indicated by way of example and are not in any way limitative.

Advantageously, the energy of the activation beam is adapted as a function of the physicochemical properties (ionisation energy, electron bond energy, electronic affinity) of the precursor ion of the ionised species of interest, in order to produce a particular product-ion, specific to the ionised species of interest.

The invention also relates to a mass spectrometry device comprising a source of ionisation adapted to form a precursor ion of an ionised species of interest from a complex mixture, the ionisation of said complex mixture producing said precursor ion of said ionised species of interest and at least one other interfering ionised species having a same predetermined mass-to-charge ratio m/z, where m represents the mass and z the electric charge number of the precursor ion of the ionised species of interest.

According to the invention, the mass spectrometry device comprises:
coupling means between an activation cell or a region of a mass spectrometer adapted to receive, on the one hand, said precursor ion of the ionised species of interest and said at least one other interfering ionised species of same mass-to-charge ratio coming from the ionisation of the complex mixture and, on the other hand, a beam of neutral species, photons, electrons or ions, said beam having an energy and an activation power that are predetermined as a function of the physicochemical properties of the precursor ion, said beam being adapted to form, by electric charge transition and with no fragmentation of the precursor ion of said ionised species of interest, a product-ion having the same mass m as the precursor ion of said ionised species of interest and an electric charge number z' such that z' is a non-zero integer number different from z, z' being preferably chosen among z+1, z+2, z+3, z−1, z−2, z−3 so that the product-ion of said ionised species of interest has another mass-to-charge ratio m/z', said other mass-to-charge ratio m/z' being different from said mass-to-charge ratio of another product-ion stemming from said at least one other interfering ionised species;
a mass analyser adapted to separate said product-ion having said other predetermined mass-to-charge ratio (m/z) specific to the ionised species of interest; and
a detection system adapted to detect selectively said product-ion having said other predetermined mass-to-charge ratio (m/z) specific to the ionised species of interest.

According to a particular aspect of the mass spectrometry device, the detection system is configured to measure the quantity of product-ion having undergone an additional ionisation with no fragmentation or an additional detachment of electron(s) with no fragmentation.

The spectrometry device of the invention allows to measure the abundance of at least one product-ion having undergone a modification of electric charge (by ionisation, electron detachment, electron capture or electron transfer) with no fragmentation as a function of the evolution of the abundance of the target precursor ion.

The invention also relates to the application of the method for mass spectrometry measurement of molecular species in a complex mixture according to one of the described embodiments to the dosage of proteins, biopolymers, polymers, macromolecules, virus, nanoparticles, micro-organisms, supramolecular assemblies or biopolymers assemblies.

In a particular and advantageous manner, the detection system is configured to measure the quantity of product-ion having undergone an additional ionisation with no fragmentation or an additional electron detachment with no fragmentation.

The invention will find a particularly advantageous application in the mass spectrometry applied to complex molecules, macromolecules and supramolecular assemblies, virus, nanoparticles or micro-organisms.

The invention advantageously allows to identify and quantify molecular species by mass spectrometry without requiring to fragment the target molecular species.

The present invention also relates to the characteristics that will be revealed during the following description and that will have to be considered in isolation or according to all their technically possible combinations.

This description given by way of non-limitative example will allow to better understand how the invention may be performed with reference to the appended drawings, in which.

The principle of the invention is based on the SRM or MRM method, but does not lie on the detection of fragmentations induced in the tandem spectrometry step(s) but rather on the observation of intact molecular ions but that have undergone one (or several) ionisation(s), one (or several) electron detachment(s), one (or several) electron capture(s), or one (or several) electron transfer(s) according to whether the precursor ion is positive or negative.

Hence, in the case of a negative precursor ion, or precursor anion, of charge z higher than or equal to two, the activation of this precursor anion may lead to the detachment of electron(s) according to the equation of detachment of one electron:

$$M^{z-} \rightarrow M^{(z-1)-} + e^- \quad\quad 1.$$

This activation, shown by an arrow, may be performed by impact of electrons, collision with neutral species, collision with ions or absorption of photon(s) coming from a laser, a lamp, a synchrotron radiation or a free electron laser.

In this case, it is necessary that the charge of the precursor anion is higher than or equal to two so as to keep at least one negative charge on the product-ion of the reaction to allow the detection thereof by mass spectrometry.

Figure 2:
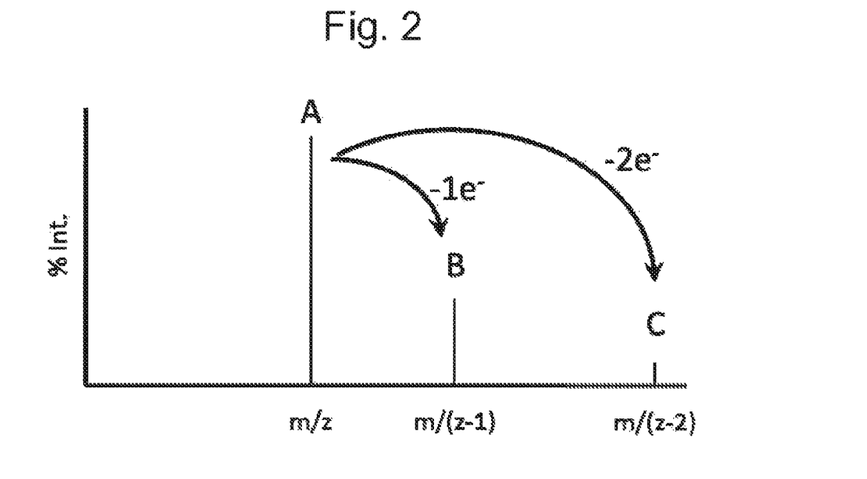
FIG. 2 schematically shows an example of tandem mass spectrum of negative ion electron detachment.

By way of illustration, it has been shown in FIG. 2 a tandem mass spectrum after, for example, the photo-detachment of one or two electrons of a negative ion. The precursor anion A has a mass-to-charge ratio m/z. By absorption of a photon radiation having an energy higher than or equal to the energy required to tear off an electron (10) from the precursor anion A, an new product-anion B is obtained, which has one electron less than the precursor anion A and has hence a mass-to-charge ratio equal to m/(z−1), where z represents the electric charge number of the precursor anion A. Due to the fact that the product-anion B has one electron less than the precursor anion A, the charge of the product-anion B is lower by one unit than the charge of the precursor anion A. It may also be obtained a new product-anion C that has two electrons less than the precursor anion A during the same sequence of activation. The product-anion C has hence a mass-to-charge ratio equal to m/(z−2). The product-anion C may be obtained by simultaneous tear-off of two electrons from the precursor anion A or by tear-off of one electron from the product-anion B.

In a variant, the product-anions B and C may be produced by electron transfer towards a cation in a mechanism called N-ETD (Negative Electron Transfer Dissociation).

In the case where a positive precursor ion, or precursor cation, of charge z higher than or equal to one, the activation by charge transition may lead to the ionisation of this cation with increase of its charge according to the equation of ionisation:

$$M^{z+} \rightarrow M^{(z+1)+} + e \quad\quad 2.$$

Likewise, this activation, represented by an arrow, may be performed by impact of electrons, collision with neutral species, collision with ions or absorption of photon(s) coming from a laser, a lamp, a synchrotron radiation or a free electron laser.

Figure 3:
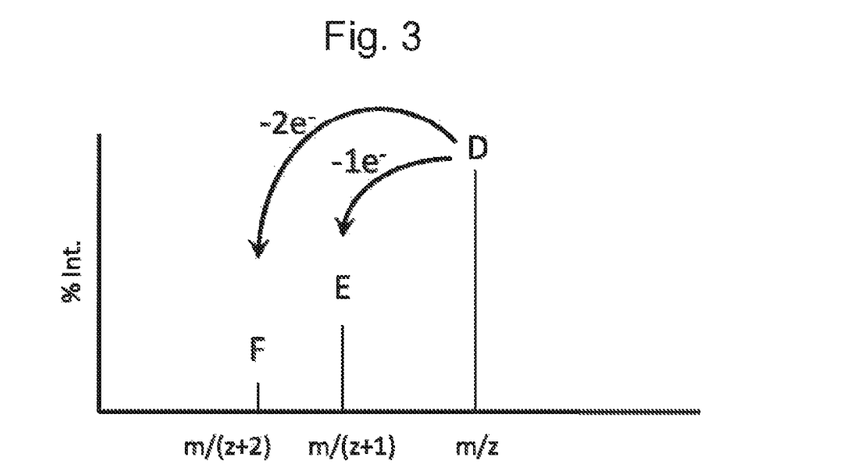
FIG. 3 schematically shows an example of tandem mass spectrum of positive ion ionisation.

Similarly to FIG. 2, it has been shown in FIG. 3 an example of a tandem mass spectrum of positive ion photo-ionisation. The precursor cation D has a mass-to-charge ratio m/z. By absorption of a photon radiation having an energy higher than or equal to the energy required to induce an ionisation (110) of the precursor cation D, a new product-cation E is obtained, the loss of one electron of which leads to an additional positive charge with respect to the precursor cation D and with hence a mass-to-charge ratio equal to m/(z+1), where z represents the electric charge number of the precursor cation D. Similarly, by interaction with a beam of photons or electrons, a new product-cation F may also be formed, which has two positive electronic charges more than the precursor cation D. The product-cation F has hence a mass-to-charge ratio equal to m/(z+2). The product-cation F may be obtained by simultaneous tear-off of two electrons from the precursor cation D or by tear-off of one electron from the product-cation E.

In a variant, the precursor cation of ratio m/z of charge z higher than 2 may also undergo an electron capture (ECD) or an electron transfer (ETD), by interaction with an electron beam or with an anion beam, respectively, to form a new product-cation of charge (z−1) and of ratio m/(z−1). Although relating to cations, this variant is similar to the case presented in FIG. 2.

It is hence observed that the reaction of electron detachment generates product-anions B, C that are offset towards the increasing ratio m/z for a precursor-anion. On the contrary, the reaction of ionisation generates product-cations E, F that are offset towards the decreasing ratio m/z for a precursor cation. The reaction of activation by electron tear-off or by ionisation of the precursor ions induces a different modification of the mass spectrum according to the polarity of the precursor ions and the method of activation. Complementarily, it may allow to determine the state of charge of the precursor ion or target ion.

The activation by electric charge transition of the precursor ion, or target ion, may be produced by impact of electrons, collision with neutral species, collision with ions or absorption of photon(s) coming from a laser, a lamp, a synchrotron radiation or a free electron laser and directed to the precursor ion.

For that purpose, after the source of ionisation and after the step of selection, it is added to the precursor ion a sufficient energy to tear off one or several electrons or a sufficient energy to induce an additional ionisation of the precursor ion by capture of one or several electrons.

According to the means of activation and the time of activation involved, the reactions of ionisation and/or electron detachment may lead to the emission of several electrons either directly, or sequentially according to one of the following equations, respectively:

$$M^{z+} \rightarrow M^{(z+n)+} + ne^-$$  3. Multiple ionisation $$M^{z-} \rightarrow M^{(z-n)-} + ne^-$$  4. Multiple electron detachment The reactions 1 to 4 have the particularity to give a product-ion whose mass-to-charge ratio is specific to determined mass and charge of the precursor ion, hence a precise mass-to-charge ratio, which allows to analyse in a non-ambiguous manner a particular molecular species at the origin of the precursor ion.

By way of non-restrictive example, the analysis of polypeptides by simple MS may be made difficult by the presence of interfering ions whose ratio m/z is identical or very close to those of the species of interest, but whose mass and charge are different. The application of the method proposed in the invention allows to suppress these ambiguities. Indeed, the analysis of a particular transition of charge according to one or several of the reactions 1 to 4 gives a product-ion specific to the ratio m/z of the polypeptide and that is different from those of the interfering ions of the complex matrix.

By way of non-restrictive example, the SRM or MRM dosing of a protein of interest in a complex mixture of proteins requires to pass by a step of enzymatic digestion of the medium containing all the proteins. In conventional SRM (or MRM), one (or several) particular transitions are followed up for one or several peptides stemming from the proteolytic digestion of the protein of interest. Nevertheless, the digestion of other proteins present in the medium may generate proteolytic peptides that interfere with the conventional SRM or MRM measurement (either because these peptides are identical to those that are looked at or because they give identical transitions). The application of the method proposed herein is not sensitive to these problems of interference, because it is specific to the protein of interest. Hence, the proteins of the medium may have ratios m/z that are very close to each other, or even indiscernible from that of the precursor ion of interest. However, the follow-up of one or several charge transitions according to the equations 1 to 4 gives one or several product-ion(s) specific to the ratio m/z of the species of interest.

This method may be applied, by way of non-restrictive example, to the dosage of other entire biomolecules, non-covalent complexes and assemblies, synthetic polymers, nanoparticles, virus or other micro-organisms, etc. Indeed, certain precursor ions cannot be fragmented or are difficult to fragment by the conventional methods of activation and can hence not be subjected to a SRM (or MRM) analysis. Nevertheless, these objects may undergo charge transitions, which make the proposed method applicable and allows the dosage thereof.

In particular, in the case of a complex mixture containing the ion of interest and an interfering ion of same mass-to-charge ratio (m/z), the ionisation, the electron detachment, the electron capture or transfer, lead to specific product-ion coming from the reaction on the precursor ion of interest, which are different from the product-ions stemming from reactions coming from the interfering ions, which allows to separate the contributions of the precursor ions of interest from those of the interfering ions. Hence, the energy of activation or excitation is not necessarily specific to a species of interest and the contaminants may also undergo charge transitions during the activation, however the mass-to-charge ratios of the product-ions stemming from these reactions are different for the species of interest and for the interfering ions, respectively.

Moreover, the ionisation and the electron detachment cannot be considered as fragmentations, because the mass of the precursor ions is not affected but only the charge thereof. Let's note (m/z) the mass-to-charge ratio of the precursor ion of interest and (m'/z') the mass-to-charge ratio of an interfering ion or contaminant. Let's suppose that (m/z) is equal to (m'/z') whereas the mass m of the precursor ion is different from the mass m' of the interfering ion and the electric charge number z of the precursor ion is different from the electric charge number z' of the interfering ion. The conventional mass spectrometry does not allow to distinguish the precursor ion from the interfering ion due to the fact that (m/z) is equal or very close to (m'/z'). However, following an activation inducing an ionisation or an electron detachment, these two ionic species give different product-ions.

In the case of positive ions, having different charges z and z', it is obtained:
m/z→m/(z+1) for the precursor ion of interest
m'/z'→m'/(z'+1) for the interfering ion.

Hence, even if the contaminant has a mass-to-charge ratio indiscernible from that of the precursor ion of interest (m/z equal or very close to m'/z'), after reaction (charge transition), the product-ion has a mass-to-charge ratio m/(z+1) different from m'/(z'+1).

Likewise, in the case of anions:
m/z→m/(z−1) m'/z'→m'/(z'=1)
where m/(z−1) is different from m'/z'−1).

In the case of multiple ionisation or multiple electron detachment reactions, the transitions produce ionic species having a mass-to-charge ratio: m/(z+1), m/(z+2) or m/(z+3) . . . for positive ions and respectively ionic species having a mass-to-charge ratio: m/(z−1), m/(z−2), m/(z−3) . . . for negative ions.

The detection of ionic species of ratio: m/(z+1), m/(z+2) or m/(z+3) for positive ions, m/(z−1), m/(z−2), m/(z−3) . . . for negative ions can serve within the framework of a MRM-type analysis.

The method of tandem mass spectrometry by charge transition has many advantages. The ionisation, the electron detachment, the electron capture or transfer may occur on entire ionised species, or even directly on non-covalent assemblies. The method of the invention allows to make the analysis of entire biopolymers (proteins, nucleic acids . . . ) without passing by a step of digestion contrary to the techniques of analysis based on the fragmentation. The proposed method hence allows the direct analysis of ionised molecular species of any size.

Moreover, this method is applicable to species that cannot be fragmented, as the nanoparticles, the virus or any other type of cells or assemblies of biopolymers or cells as long as they can be placed in gaseous phase in a mass spectrometer.

The mass spectrometry method is not specific to a particular activation means. Indeed, the ionisation or the electron detachment can have for origin the impact of electrons, the energetic collisions with neutral species, the collisions with ions or the absorption of photon(s) stemming from a laser source, a lamp, a synchrotron radiation, or a free electron laser. The electron capture leading to a reduction of the charge may also occur following the interaction with an electron beam. The electron transfer leading to a modification of the charge may also occur following the interaction with a reactive ion.

This method may be implemented on a variety of existing instruments of mass spectrometry.

Figure 4:
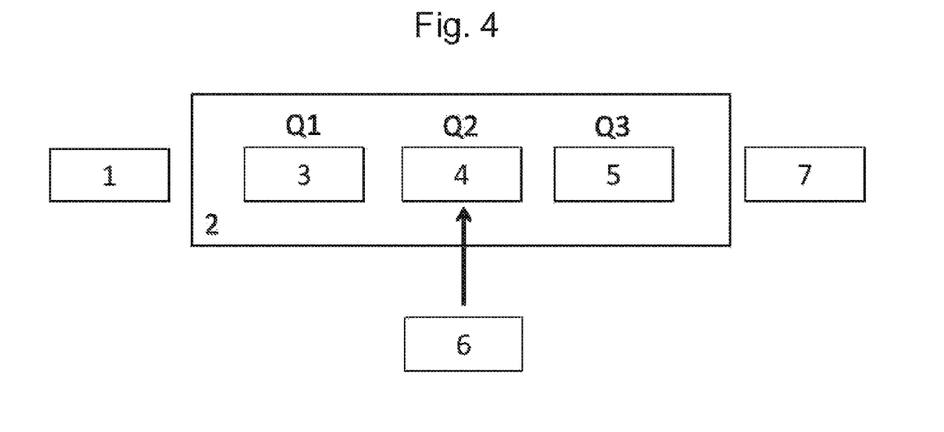
FIG. 4 schematically shows a triple-quadrupole mass spectrometer according to an embodiment of the invention.

In FIG. 4 is shown an example of a triple-quadrupole mass spectrometry system according to an embodiment of the invention.

The mass spectrometry device of FIG. 4 comprises an ion source 1, a mass spectrometry 2 and an ion detection system 7. The mass spectrometer 2 is coupled at the input to the ion source 1 to receive the ionised species stemming from the source. The mass spectrometer 2 is coupled at the output to the ion detection system 7, which detects the ions separated by the analyser of the mass spectrometer as a function of their mass-to-charge ratio. Moreover, the mass spectrometer 2 is coupled to a source 6 of electromagnetic radiation (laser, ultra-violet lamp, synchrotron radiation) or to an electron beam (electron gun). In the example of FIG. 4, the mass spectrometer 2 is of the triple quadrupole type and comprises a first quadrupole Q1, a second quadrupole Q2 and a third quadrupole Q3. The first quadrupole Q1 allows to select a domain of ratio m/z centred on the ratio m/z of the precursor ion of interest. The second quadrupole Q2 is coupled to a source 6 of electromagnetic radiation (laser, UV lamp, synchrotron radiation) or to an electron beam. The second quadrupole Q2 serves as an activation cell and comprises a region of activation 4 of the precursor by interaction with the photon or electron beam so as to induce an ionisation or an electron detachment of the precursor ion. The third quadrupole Q3 allows to filter the ions having undergone a charge transition of interest as a function of their mass-to-charge ratio (m/z').

The mass spectrometer is hence configured to extract, towards the detection system, a product-ion having undergone a specific charge transition with no fragmentation to allow the detection of this specific product-ion.

The detection system 7 is adapted to allow the detection and the measurement of the different product-ion(s) having undergone one or respectively several charge transition of interest.

The detection system 7 provides, after a suitable signal processing, a mass spectrum. The so-obtained mass-spectrum allows to provide new information about the molecular species of origin.

Advantageously, the mass spectrometry device comprises means for detecting a precursor ion having a predetermined mass-to-charge ratio (m/z) and means for detecting a product-ion having a mass-to-charge ratio (m/z') such that said product-ion has the same mass m as said precursor ion and an electric charge number z' such that z' is a non-zero integer number chosen among z+1, z+2, z+3, z−1, z−2, z−3.

Figure 5:
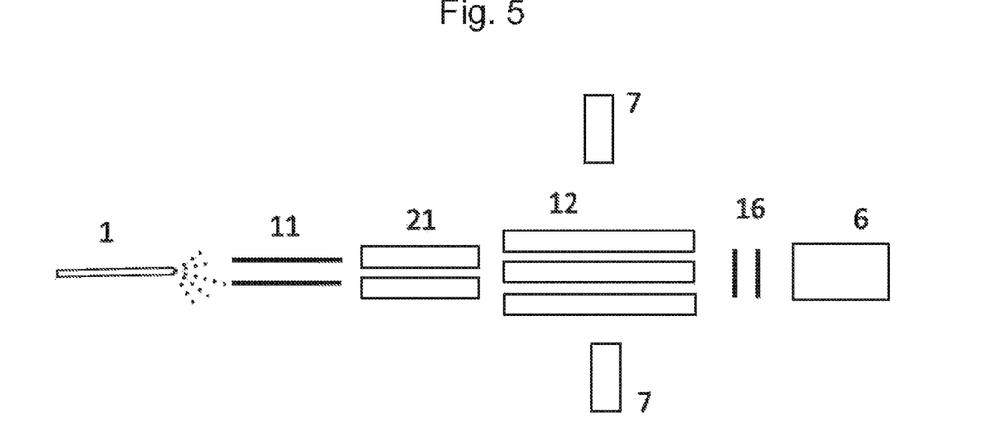
FIG. 5 schematically shows an example of device based on the use of an ion trap coupled to a source of electromagnetic radiation.

In FIG. 5 has been shown another example of device based on the use of an ion trap coupled to a source of electromagnetic radiation. The device of FIG. 5 comprises an ion source 1, an ion transfer capillary 11, an ionic optical system 21, a linear quadrupole ion trap 12, an ion detection system 7, a VUV lamp, for example a neon discharge lamp producing photons of about 16 eV, or a helium discharge lamp producing photons of about 21.22 eV, a laser 6 or the synchrotron radiation and, optionally, a shutter 16 for shutting the light beam 26 emitted by the laser 6.

The ion source 1 generates at least one gaseous-phase precursor ion from an analyte. The ion transfer capillary 11 allows to transfer the gaseous-phase ionised species from the ion source towards the ion trap 12. The ionic optical system 21 focuses the ions in an area of the electromagnetic field of the linear quadrupole ion trap 12, where the precursor ion is trapped.

The optional shutter 16 being open, the laser beam 36 emitted by the laser 6, the discharge lamp or the synchrotron radiation may hence interact in the ion trap 12 with the precursor ion.

Typically, in the case of negative precursor ions, a photon beam having an energy of 4 eV or more may lead to the detachment of electrons [Antoine R and Dugourd P 2011 Visible and ultraviolet spectroscopy of gas phase protein ions Phys. Chem. 13, 16494]. A beam of electrons having an energy higher than 10 eV may lead to the electron detachment [Zubarev R A 2003 Reactions of polypeptide ions with electrons in the gas phase. Mass spectrometry Reviews 22 57-77]. Typically, in the case of positive ions, photons having an energy higher than 10 eV may lead to the photo-ionisation according to the state of charge of the precursor [Giuliani A, Milosavljević A R, Hinsen K, Canon F, Nicolas C, Réfrégiers M and Nahon L 2012 Structure and Charge-State Dependence of the Gas-Phase Ionization Energy of Proteins Angewandte Chemie International Edition 51 9552-6]. Typically, an electron beam having an energy higher than about 10 eV may lead to the ionisation of the precursor according to the state of charge of the precursor [Fung Y M E, Adams C M and Zubarev R A 2009 Electron Ionization Dissociation of Singly and Multiply Charged Peptides J. Am. Chem. Soc 131 9977-85; Zubarev R A and Yang H 2010 Multiple Soft Ionization of Gas-Phase Proteins and Swift Backbone Dissociation in Collisions with ≤99 eV Electrons Angewandte Chemie International Edition 49, 1439-1441].

The one skilled in the art will adapt the flow of photons of the photon source and/or its power and wavelength as a function of the energy required for an ionisation, an electron detachment according to certain physicochemical properties of the target ion, in particular the photo-absorption cross section of the target ion. The one skilled in the art will adapt the kinetic energy of the electrons as a function of the energy required to be added to the system to produce an electron detachment or ionisation according to certain physicochemical properties of the target precursor ion.

The ion trap is configured to extract product-ions corresponding to a particular charge transition and having not undergone fragmentation. Knowing the mass-to-charge ratio (m/z) of the precursor ion, the detection system 7 detects specifically the so-activated ionised species, or product-ions, having a mass-to-charge ratio equal to (m/z) such that (m/z) of the product-ion is equal to (m/(z−1)), (m/(z−2)), (m/(z−3)) or (m/(z+1)), (m/(z+2)), (m/(z+3)).

The ion detection system 7 is configured to measure the ions having a mass-to-charge ratio that is determined or located in a range comprised between a minimum ratio and a maximum ratio. It is hence possible to select the product-ions having a well-determined mass-to-charge ratio equal to m/(z−1) and/or to m/(z−2).

To stop the activation of the ions, it is just necessary to close the shutter 16, to stop the electron gun or to cut any beam of particles interacting with the ions of interest. A mass spectrum of non-activated molecular species and another mass spectrum of the activated molecular species can then be obtained.

Preferably, the mass analyser located after or about the region of activation of the ions and/or the detection system are configured to filter the other products of the activation by impact of a photon or electron beam with the target molecular species.

It is noted that the interaction of the analyte with a photon or electron beam may generate simultaneously fragment ions of lower mass and hence having a mass-to-charge ratio different from that of the product-ions stemming from the reactions of ionisation or electron tear-off that occur with conservation of the mass of the precursor ion. Advantageously, these fragment ions are filtered by the mass analyser located between the activation cell and the detection system.

The device and the method of the invention may be easily implemented on existing mass spectrometry devices.

In particular, the device and the method exposed herein are compatible with any instrumental arrangement in which the steps b) of activation and c) of production-ion separation are performed. It can be mentioned in particular by way on non-limitative example: a quadrupole-time-of-flight spectrometer comprising a region of activation, a quadrupole-ion trap spectrometer, a triple quadrupole spectrometer, a time-of-flight-time-of-flight (Tof-Tof) spectrometer or a hybrid-orbitrap spectrometer.

The invention advantageously applies to the dosing, by mass spectrometry, of any ionised molecular species in complex mixture that is impossible or difficult to fragment, by the usual techniques of activation, but for which it is possible to produce one or several charge transitions by interaction with a beam of neutral species, ions, electrons or photons.

A possible application of the method relates to the identification and the dosage of entire proteins. By way of example, we have compared the conventional SRM and MRM method with the herein proposed method of activation by charge transition with no fragmentation of the precursor ion in complex mixture.

We have taken a total extract of protein of the *E. Coli* bacterium in which we have added bovine serum albumin (BSA). This protein cannot be present in the bacterial lysate, the interferences potentially observed are hence fortuitous and come from bacterial proteins.

Figure 6:
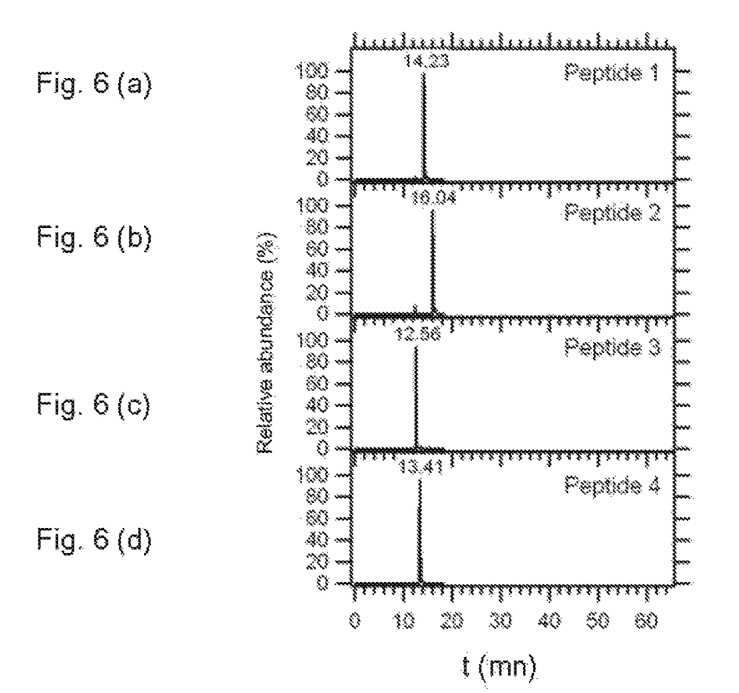
FIG. 6 shows the chromatograms obtained by a conventional SRM method for four peptides stemming from the tryptic digestion of the BSA (bovine serum albumin) protein.

In a first experiment, we have applied the conventional SRM protocol for the dosage of the BSA as described in the literature. A standard BSA digest (Protéabio) has been analysed by liquid chromatography-mass spectrometry coupling. For the SRM approach, the four most-abundant peptides, whose masse-to-charge ratios (m/z) are the following, respectively: 582.55 (peptide 1), 740.61 (peptide 2), 927.5 (peptide 3) and 941.33 (peptide 4) have been selected. Two transitions have been chosen for each peptide with a width of selection and detection of 1 Da among the most intense fragmentations obtained by collision induced dissociation (CID) for 30 ms and 35% of activation energy; those dissociations leading to peaks in the mass spectrum, respectively: 573.06-574.06 and 950.86-951.86 (peptide 1), 812.96-813.96 and 1017.02-1018.02 (peptide 2), 892-893 and 909.92-910.92 (peptide 3), 931.69-932.69 and 1637.13-1638.13 (peptide 4). FIGS. 6(a), 6(b), 6(c), 6(d) represent the chromatograms of extracted ions corresponding to the peptides 1, 2, 3 and 4, respectively, obtained as a function of the time of retention in the chromatography column. The time of retention that corresponds to the time taken by a product to be eluted from the chromatography column is measured. The times of retention obtained for each peptide are indicated in FIG. 6, for a column C18 (Gemini from Phenomenex, 3 μm, 110 Å, 100×2 mm) in a gradient acetonitrile-water of 60 minutes at 200 μL/min for 150 pmol injected.

Figure 7:
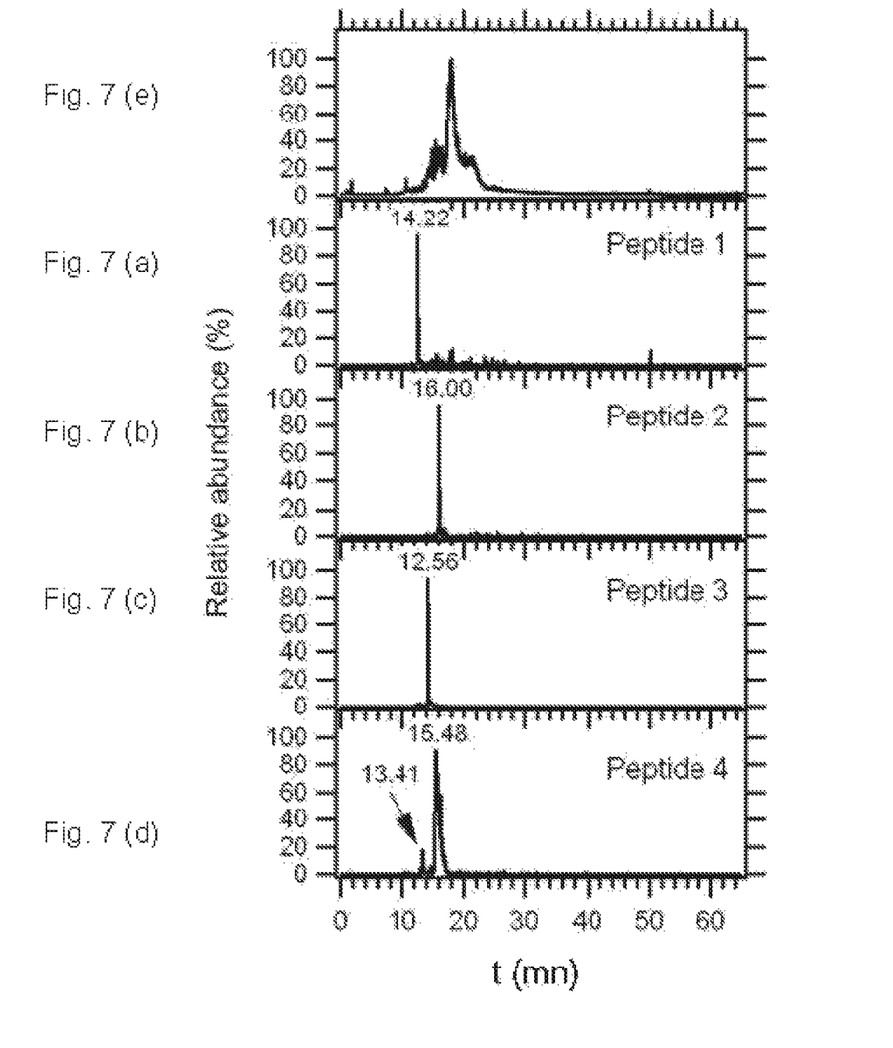
FIG. 7 shows the chromatograms obtained by a conventional SRM method for four peptides resulting from the digestion of a BSA protein in mixture with the tryptic digestion of a total extract of protein of the E. Coli bacterium.

In a second experiment, the bacterial lysate has been digested by trypsin and 5 pmol of the standard BSA digest has been added. The conventional SRM process has been applied to the detection of the BSA peptides in the same chromatographic conditions as in FIG. 6, and the results are presented in FIG. 7.

In FIG. 7(e) has been shown the total ionic current stemming from the ionisation of all the peptides present in the mixture, as a function of the time of retention. In FIGS. 7(a), 7(b), 7(c), the peptides 1, 2 and 3 are found at the same times of retention, but not the peptide 4. For the latter, in FIG. 7(d), one or several other species disturb the measurement and hence distort the detection.

Figure 8:
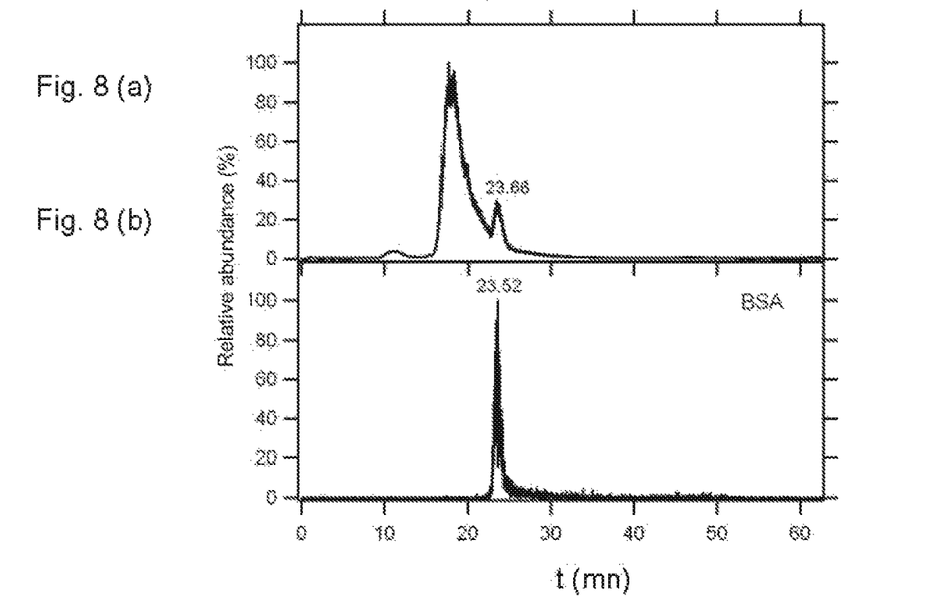
FIG. 8 shows the chromatograms obtained by SRM analysis with charge transition with no fragmentation, applied to a standard of entire BSA mixed with a raw bacterial total extract.

In a third experiment, the SRM analysis with charge transition with no fragmentation has been applied to a standard of entire BSA mixed with the total raw bacterial extract. The electrospray spectrum of the BSA contains very numerous states of charge, and the state of charge +48 giving an m/z 1384.83 has been chosen. For the analysis, the three charge transitions having a mass-to-charge ratio (with a width of 5 Da): 1301.08-1306.08 (state of charge +49), 1327.08-1332.08 (state of charge +50) and 1354.17-1359.17 (state of charge +51), respectively, have been selected. These three transitions of charge are produced by irradiation of a photon beam at 21.22 eV. FIG. 8 shows the chromatogram of the bacterial extract to which 18 pmol of BSA have been added. FIG. 8(a) shows the trace of the total ionic current due to the ionisation of all the protein present in the medium. The BSA has been eluted at 23.52 minutes by a separation in a column C18 (Gemini from Phenomenex, 3 μm, 110 Å, 100×2 mm) in a gradient acetonitrile-water of 60 minutes at 200 μL/min. In FIG. 8(b), it can be noticed that the chromatogram of the BSA does not suffer from any interference. The surface area of the chromatographic peak may be easily measured and linked to the quantity of protein added to the medium.

From this comparison between the conventional SRM (or MRM) method and the SRM (or MRM) method by transition of charge with no fragmentation, the following advantages result:

the method by transition of charge requires no enzymatic digestion of the sample. It is hence more universal and may be applied to all the proteins, in particular those which resist to the digestions (proteins rich in proline, membranous proteins . . . );

the relation between the surface area of the peaks of elution and the quantity of material injected is direct and does not require to combine several chromatographic traces;

the method by transition of charge is specific to an ionised species of interest and undergoes no interference caused by proteins of the matrix;

knowing the mass-to-charge ratio of the precursor ion, it is possible to calculate a priori the transitions of charge that will be given by said precursor ion.

The invention claimed is:

1. A method for mass spectrometry measurement of molecular species in a complex mixture, the method comprising the following steps:
   a. ionising an analyte in complex mixture to form a precursor ion (A, D) of an ionised species of interest and at least one interfering ion coming from the complex mixture, the precursor ion (A, D) of said ionised species of interest and said at least one interfering ion having a same mass-to-charge ratio m/z, where m represents the mass and z the electric charge number of the precursor ion (A, D) of said ionised species of interest;
   b. activating the precursor ion (A, D) of said ionised species of interest and of the at least one interfering ion of same mass-to-charge ratio, by interaction with a beam of neutral species, ions, electrons or photons, having a predetermined energy as a function of the energy of ionisation of the precursor ion (A, D) of said ionised species of interest or of the energy required for the detachment of electron from the precursor ion (A, D) of said ionised species of interest, said activation being adapted to produce a product-ion (B, C, E, F), by charge transition with no fragmentation of the precursor ion (A, D) of said ionised species of interest, the product-ion (B, C, E, F) having the same mass m as the precursor ion (A, D) of said ionised species of interest and an electric charge z' such that z' is a non-zero integer number different from z;
   c. separating the product-ion (B, C, E, F) of the ionised species of interest having said predetermined mass-to-charge ratio m/z' specific to the ionised species of interest;
   d. selectively detecting the product-ion (B, C, F, E) of the ionised species of interest having said predetermined mass-to-charge ratio m/z' specific to the ionised species of interest.

2. The measurement method according to claim 1, including an additional step e) after the step d), the step e) comprising a measurement of the abundance of the product-ion (B, C, E, F) having said predetermined mass-to-charge ratio m/z' specific to the ionised species of interest.

3. The measurement method according to claim 1, wherein said precursor ion (D) of the ionised species of interest has a positive polarity and the step b) of activation comprises a step of ionisation with no fragmentation so as to produce a product-ion (E, F) having the same mass m as said precursor ion (D) of the ionised species of interest.

4. The method of claim 3, wherein the product-ion (E, F) has a positive polarity such that the electric charge number z' of the product-ion (E, F) is equal to z+1 by simple ionisation, or respectively to z+2 by double ionisation.

5. The measurement method according to claim 1, wherein said precursor ion (A) of the ionised species of interest has a negative polarity and the step b) of activation comprises a step of detachment of electron(s) with no fragmentation so as to produce a product-ion (B, C) having the same mass m as said precursor ion (A) of the ionised species of interest.

6. The method of claim 5, wherein the product-ion (B, C) has a negative polarity such that the electric charge number z' of the product-ion is equal to z−1 by simple electron detachment, or respectively to z−2 by double electron detachment.

7. The measurement method according to claim 1, wherein said precursor ion (D) of the ionised species of interest has a positive polarity and the step b) of activation comprises a step of electron capture or of electron transfer with no fragmentation so as to produce a product-ion (E, F) having the same mass m as said precursor ion (D) of the ionised species of interest.

8. The method of claim 7, wherein the product-ion (E, F) has a positive polarity such that the electric charge number z' of the product-ion (E, F) is equal to z−1 by simple electron capture or transfer, or respectively to z−2 by double electron capture or transfer.

9. The measurement method according to claim 1, wherein said precursor ion (A) of the ionised species of interest has a negative polarity and the step b) of activation comprises a step of electron transfer with no fragmentation so as to produce a product-ion (B, C) having the same mass m as said precursor ion (A) of the ionised species of interest.

10. The method of claim 9, wherein the product-ion (B, C) has a negative polarity such that the electric charge number z' of the product-ion is equal to z−1 by simple electron transfer, or respectively to z−2 by double electron transfer.

11. The measurement method according to claim 1, further comprising the following steps:
    a step a1) after the step a) of ionisation, the step a1) comprising the detection and the recording of a reference mass spectrum;
    a step c1) of detection and recording of a tandem mass spectrum relating to a reference precursor ion of ratio $(m/z)_{ref}$ giving at least one product-ion (B, C, E, F) of mass-to-charge ratio (m/z'); and
    a step d1) of measurement of the abundance of the product-ion (B, C, E, F) of the ionised species of interest.

12. The measurement method according to claim 11, wherein the step b) of activation is performed by interaction of a precursor ion (A, D) with a photon beam stemming from a laser (6), a discharge lamp or a synchrotron radiation source or an electron beam.

13. The measurement method according to claim 11, wherein the step b) of activation is performed by interaction of a precursor ion (A, D) with a photon beam having an energy comprised between 3 eV and 40 eV.

14. The measurement method according to claim 11, wherein the step b) of activation is performed by interaction of a precursor ion (A, D) with a photon beam having a kinetic energy comprised between 0 and 100 eV.

15. The measurement method according to claim 11, wherein the step b) of activation is performed by interaction of a precursor ion (A, D) with a beam (26) of energetic ions having an energy comprised between 0.1 and 10 keV.

16. The measurement method according to claim 1, wherein the steps b) of activation and c) of separation of a product-ion are performed in an ion trap (12).

17. An application of the method for mass spectrometry measurement of molecular species in a complex mixture according to claim 1 to the dosage of proteins, biopolymers, polymers, macromolecules, virus, nanoparticles, micro-organisms, supramolecular assemblies or biopolymers assemblies.

18. The method of claim 1, wherein z' is chosen among z+1, z+2, z+3, z−1, z−2, z−3, so that the product-ion (B, C, E, F) of said ionised species of interest has a mass-to-charge ratio m/z' different from the mass-to-charge ratio of the product-ion(s) stemming from the activation of the at least one interfering ion.

19. A mass spectrometry device comprising:
a source of ionisation (1) adapted to form a precursor ion (A, D) of an ionised species of interest from a complex mixture, the ionisation of said complex mixture producing said precursor ion (A, D) of said ionised species of interest and at least one other interfering ionised species having a same predetermined mass-to-charge ratio m/z, where m represents the mass and z the electric charge number of the precursor ion (A, D) of the ionised species of interest;
the mass spectrometry device comprising:
coupling means between an activation cell (12, Q2) or a region of a mass spectrometer adapted to receive, on the one hand, said precursor ion (A, D) of the ionised species of interest and said at least one other interfering ionised species of same mass-to-charge ratio coming from the ionisation of the complex mixture and, on the other hand, a beam of neutral species, photons, electrons or ions, said beam having an energy and an activation power that are predetermined as a function of the physicochemical properties of the precursor ion (A, D), said beam being adapted to form, by electric charge transition and with no fragmentation of the precursor ion of said ionised species of interest, a product-ion (B, C, E, F) having the same mass m as the precursor ion of said ionised species of interest and an electric charge number z' such that z' is a non-zero integer number different from z; and
a mass analyser adapted to separate said product-ion (B, C, E, F) having said other predetermined mass-to-charge ratio (m/z') specific to the ionised species of interest; and
a detection system (7) adapted to selectively detect said product-ion (B, C, E, F) having said other predetermined mass-to-charge ratio (m/z') specific to the ionised species of interest.

20. The mass spectrometry device according to claim 19, wherein the detection system (7) is configured to measure the quantity of product-ion (B, C, E, F) having undergone an additional ionisation with no fragmentation or an additional electron detachment with no fragmentation.

* * * * *